(12) United States Patent
Chaney et al.

(10) Patent No.: US 7,815,922 B2
(45) Date of Patent: Oct. 19, 2010

(54) ARTICLES HAVING BIOACTIVE SURFACES AND SOLVENT-FREE METHODS OF PREPARATION THEREOF

(75) Inventors: Bryce Chaney, Durham, NC (US); David Montgomery, Cary, NC (US); Ross W. Jacobson, Hillsborough, NC (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 1526 days.

(21) Appl. No.: 11/129,318

(22) Filed: May 16, 2005

(65) Prior Publication Data

US 2005/0255327 A1 Nov. 17, 2005

Related U.S. Application Data

(60) Provisional application No. 60/570,816, filed on May 14, 2004.

(51) Int. Cl.
*A61K 9/00* (2006.01)
*A61K 31/74* (2006.01)
*A61K 47/48* (2006.01)
*A61F 2/00* (2006.01)
*A61K 47/30* (2006.01)
*C23C 16/00* (2006.01)

(52) U.S. Cl. .................. 424/400; 424/78.17; 424/423; 514/772.1; 514/772.3; 427/2.1; 427/255.11; 427/255.6

(58) Field of Classification Search ............... 424/400, 424/486
See application file for complete search history.

(56) References Cited

U.S. PATENT DOCUMENTS

| | | | |
|---|---|---|---|
| 4,447,546 A * | 5/1984 | Hirschfeld | ................... 436/527 |
| 4,994,373 A | 2/1991 | Stavrianopoulos | |
| 5,077,210 A | 12/1991 | Eigler et al. | |
| 5,080,924 A | 1/1992 | Kamel et al. | |
| 5,474,796 A | 12/1995 | Brennan | |
| 5,624,711 A | 4/1997 | Sundberg et al. | |
| 5,688,642 A | 11/1997 | Calvert et al. | |

(Continued)

FOREIGN PATENT DOCUMENTS

EP 0 947 246 10/1999

(Continued)

OTHER PUBLICATIONS

Brahim et al., Chemical and Biological Sensors Based on Electrochemical Detection Using Conducting Electroactive Polymers, Microchim. Acta 143, 123-137 (2003).*

(Continued)

*Primary Examiner*—James D Anderson
*Assistant Examiner*—Gregg Polansky
(74) *Attorney, Agent, or Firm*—Morgan, Lewis & Bockius LLP

(57) ABSTRACT

Methods for preparing articles having a bioactive surface comprising treating a substrate to form free reactive groups, depositing a monomer onto the treated substrate, and covalently immobilizing a biologically functional molecule onto the deposited monomer. Additional embodiments include methods for the deposition of the monomer onto the treated substrate in a solvent-free environment. Further embodiments include articles having surfaces prepared using the methods described herein. Additional embodiments include articles prepared using the methods described herein.

17 Claims, 1 Drawing Sheet

U.S. PATENT DOCUMENTS

| | | | |
|---|---|---|---|
| 5,760,130 A | | 6/1998 | Trounstine et al. |
| 5,919,523 A | * | 7/1999 | Sundberg et al. .............. 506/32 |
| 6,129,956 A | | 10/2000 | Morra et al. |
| 6,270,779 B1 | * | 8/2001 | Fitzhugh et al. ............. 424/400 |
| 6,548,263 B1 | * | 4/2003 | Kapur et al. ................. 435/7.2 |
| 6,916,541 B2 | | 7/2005 | Pantano et al. |
| 2002/0000398 A1 | | 1/2002 | Skold |
| 2002/0150921 A1 | * | 10/2002 | Barany et al. |
| 2003/0224441 A1 | | 12/2003 | Nakamura et al. |
| 2004/0062882 A1 | | 4/2004 | Liebmann-Vinson et al. |
| 2004/0091604 A1 | | 5/2004 | Dempsey et al. |
| 2004/0234962 A1 | | 11/2004 | Alarcon et al. |
| 2005/0058842 A1 | | 3/2005 | Liebmann-Vinson et al. |
| 2005/0059140 A1 | | 3/2005 | Liebmann-Vinson et al. |
| 2005/0113657 A1 | | 5/2005 | Alarcon et al. |
| 2005/0113658 A1 | | 5/2005 | Jacobson et al. |

FOREIGN PATENT DOCUMENTS

| | | | |
|---|---|---|---|
| EP | 1 223 149 | | 7/2002 |
| GB | 2318791 | * | 5/1998 |
| WO | WO/98/04652 | | 2/1998 |
| WO | WO/99/40038 | | 8/1999 |
| WO | WO/01/70641 | | 9/2001 |
| WO | WO/03/022769 | | 3/2003 |

OTHER PUBLICATIONS

Spargo et al., Spatially Controlled Adhesion, Spreading, and Differentiation of Endothelial Cells on Self-Assembled . . . , Proc. Nat. Acad. Sci., USA 1994, 91, 11070-11074.

Stile, et al., Sequential Robust Design Methodology and X-Ray Photoelectron Spectroscopy To Analyze the Grafting of Hyaluronic . . . , Jrnl. Biom. Research., 2002, 61(3):391-8.

Rowley et al., Alginate Hydrogels as Synthetic Extracellular Matrix Materials, Biomaterials, 1999, 20:24-63.

International Search Report for PCT/US2005/017019 dated Jul. 11, 2006.

* cited by examiner

ARTICLES HAVING BIOACTIVE SURFACES AND SOLVENT-FREE METHODS OF PREPARATION THEREOF

CROSS-REFERENCE TO RELATED APPLICATION

This application claims the benefit of U.S. Provisional Application No. 60/570,816, filed May 14, 2004, which is incorporated herein by reference.

BACKGROUND OF THE INVENTION

1. Field of the Invention

The invention generally relates to articles having bioactive surfaces, as well as solvent-free methods of preparation. The invention more particularly relates to preparing articles having bioactive surfaces by solvent-free deposition of a monomer onto the surface of a substrate having free reactive groups, and then covalently immobilizing a biologically functional molecule onto the monomer-deposited substrate.

2. Background of the Invention

Any surface of a non-biological origin initiates a sequence of unwanted reactions when brought into contact with living tissue or blood. The most well known reactions are those generated by the blood-contacting materials that activate the platelets and the plasma coagulation system leading the formation of a thrombus. Foreign surfaces in living tissue activate the complement and the mononuclear cell systems, thereby creating inflammatory reactions. To overcome these unwanted reactions, surfaces must be rendered biocompatible, prior to the use in vivo.

The importance of biocompatible surfaces, i.e. surfaces that are stable in a biological environment, is well known and has been sought after for many years and through a variety of approaches. Biocompatible surfaces are needed for medical devices that are to be implanted for extended time periods. It is well-known that, generally speaking, biocompatibility properties are enhanced by attempting to secure biologically active agents to surfaces of medical devices, particularly those which contact tissue, including blood, when they are implanted or otherwise used during medical procedures and the like. Furthermore, it may be undesirable to have the biologically active agent leach away in wet environments, such as are encountered in blood or other body fluids.

Additionally, it is equally desirable to use biocompatible surfaces in in vitro settings. Biocompatible surfaces can be used to mimic or approximate in vivo settings, for example, to promote in vitro cell survival, proliferation or differentiation. Additionally, the biocompatible surfaces can be used in an in vitro setting to screen the effects of molecules, such as drugs, drug candidates, proteins, mutant proteins, etc. on cells or tissues, prior to the administration to a subject.

Many approaches to preparing biocompatible surfaces concentrate on utilizing polymeric surfaces as the surface which encounters the body fluids or cell culture fluids, and then treating those polymeric surfaces according to a variety of procedures. Other approaches treat metallic surfaces that are intended to contact body fluids during implantation and the like.

Generally speaking, the types of treatments that have been implemented or attempted fall into three broad categories. One involves plasma discharge treatments of the medical device surface. Another involves immersing or similar means for contacting the surface with specific chemical components under treatment conditions (such as elevated temperature), which are less elaborate than plasma discharge treatments.

The third general type of treatment typically involves chemically oxidizing the surface (usually metal), until enough of an oxide layer is provided for bonding.

Current methods for producing biocompatible surfaces utilize solution phase chemistry, where a component (monomer) that is coated onto the surface is dissolved in solvent. Solvents, however, can often times harm the surface being treated, or they can harm or denature the biologically active molecule being immobilized. For example, when plastics are being rendered biocompatible, the use of organic solvents may destroy the plastic surface.

Thus there is a need in the art for a process of treating surfaces without the use of solvent. These treated surfaces can further be rendered biocompatible for use in an in vivo or an in vitro setting.

SUMMARY OF THE INVENTION

The present invention provides articles comprising a bioactive surface, with the article comprising a substrate, a monomer-deposited layer on the substrate, where the monomer-deposited layer is of substantially uniform thickness and is substantially defect free. The surface also has and a biologically functional molecule covalently attached to the monomer-deposited layer. The substrates may comprise, for example, glass, metal, plastic ceramic or hydrogel. In one embodiment, the monomer that is deposited on the substrate is aminopropyltrimethoxysilane (APTMS), and the biologically functional molecule is hyaluronic acid.

The present invention also provides methods of making articles with bioactive surfaces. The methods of the present invention comprise treating a substrate to form free-reactive groups on the surface of the substrate, and depositing a monomer onto the treated surface in a solvent-free environment. The deposition of the monomer in a solvent-free environment results is a monomer-deposited layer that is substantially defect free and is of substantially uniform thickness. Once the monomer has been deposited onto the treated surface, a biologically functional molecule is covalently attached thereto, to provide the article with a bioactive surface. In one particular embodiment, the monomer that is deposited onto the treated substrate is APTMS. The present invention also provides articles produced by these "solvent-free" methods, where the substrate is non-metallic. In one embodiment, the methods of treating the substrate to produce free-reactive groups include plasma treatment; and the monomer is deposited onto the treated substrate via vapor deposition.

The present invention also provides articles with a bioactive surface, with the article comprising a substrate, a layer deposited on the substrate, where the layer is of substantially uniform thickness and is substantially defect free and comprises a monomer and a hydroxyl-rich polymer. The surface also has and a biologically functional molecule covalently attached to the hydroxyl-rich and monomer layer.

DETAILED DESCRIPTION OF THE INVENTION

Figure 1:
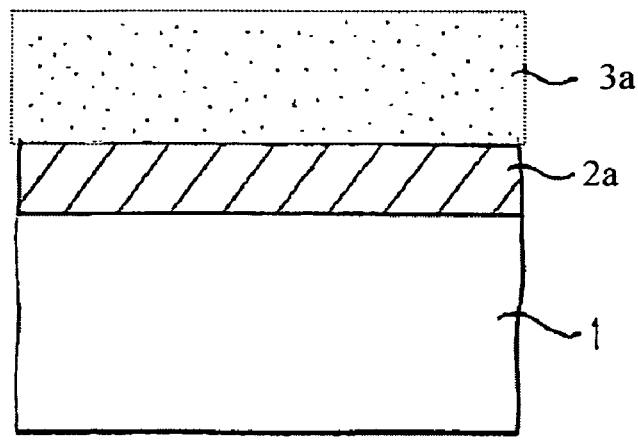
FIG. 1 depicts a side-view of an embodiment of an article of the present invention, comprising a substrate (1), a deposited monomer layer (2a), and a bioactive surface (3a).

Various embodiments disclosed herein relate to methods for preparing articles having a bioactive surface comprising treating a substrate to form free reactive groups, depositing a monomer onto the treated substrate, and covalently immobilizing a biologically functional molecule onto the deposited monomer. Additional embodiments include methods for the deposition of the monomer onto the treated substrate in a solvent-free environment. Further embodiments include articles having surfaces prepared using the methods described herein.

As used herein, a "bioactive surface" is used to mean a surface that is capable of specific interaction in a biological environment. Examples of specific interactions include, but are not limited to, the specific binding of a target molecule, such as but not limited to a cell surface marker, or analyte to one or more complementary binding partner(s), the release of an agent or molecule that has one or more specific functions in a given environment. Accordingly, articles having bioactive surfaces may be, but are not limited to, optical fibers, biosensors that detect the presence/concentration of a particular compound or chemical in a biological setting, a drug-delivery system, bioseparators that can be used as separation membranes or, for example, in dialysis, catheters, stents and other vascular grafts or prosthetics that can bind to cell surface markers or release agents in a given environment, dental implants, contact lenses, orthopedic implants and tissue culture labware, to name a few. Thus a bioactive surface may have the ability to alter or provide information about in vitro, in situ or in vivo conditions in a specific manner. Bioactive surface may comprise a material capable of receiving one or more components capable of specific interaction in a biological environment. Thus, an exemplary bioactive surface may comprise a swellable hydrogel that can receive a binding protein capable of functioning in a biosensor. As used herein, a "biological environment" is used to mean an in vivo, in situ or in vitro setting comprising or capable of supporting tissue, cells, organs, body fluids, single-celled organisms, multicellular organisms, or portions thereof. The cells, tissue, organs or organisms, etc. or portions thereof can be alive (metabolically active) or dead (metabolically inactive). Examples of biological settings include, but are not limited to, in vitro cell culture settings, in vivo settings in or on an organism (such as an implant), a diagnostic or treatment setting, tool or machine, such as a DNA microarray or blood in a dialysis machine. The type of biological environment in which the surface can be placed should not limit the present invention. The bioactive surfaces, in general, can be biocompatible in that they can be, but not need be, non-fouling, resistant to accumulation of non-specific deposits and do not initiate any appreciable immune reaction when placed in an in vivo setting.

The methods of preparing an article having a bioactive surface of the present invention involve treating a substrate to form free reactive groups. As used herein, the substrate that is used in the methods of the present invention can be any substrate that is, in whole or in part, capable of being treated to form free reactive groups. For example, the substrate may be, in whole or in part, metal or non-metal. Non-metal substrates include, but are not limited to, such substrates as glass, plastic, silicon and ceramic, to name a few. In one embodiment of the present invention, the substrate comprises glass, e.g. a glass fiber. In another embodiment of the present invention, the substrate comprises plastic. Examples of materials used in plastics include, but are not limited to, polypropylene, polycarbonate, polystyrene, polyacrylamide, polyurethane, polyester, cyclic olefinic copolymers, polymethylpentene, and polyethylene. In yet another embodiment of the present invention, the substrate comprises a metallic material, stainless steel, nickel, silver, platinum, gold, titanium, tantalum, iridium, tungsten, aluminum, nitinol, inconel, or the like. In still another embodiment, the substrate comprises other non-metal substrates, such as, but not limited to, silicon, carbon or carbon fiber, cellulose acetate, cellulose nitrate and ceramic. The substrates used in the methods of the present invention can be any shape or dimension, provided their shape or dimensions do not preclude them from being treated to form free reactive groups. For example, the substrate may be a three-dimensional construct such as a lyophilized hydrogel, or the surface of plastic or glass cell or tissue culture lab ware, or a metal stent. As should be apparent from the foregoing examples, the substrate may or may not be porous.

In one embodiment, the substrates are treated to form free reactive groups on the surface of the substrate. As used herein, "substrate" includes any two- or three-dimensional, solid or porous, support or structure. A substrate may be glass, metal, plastic, as well as a lyophilized natural or synthetic polymeric material. As used herein, "treatment" or "treating" includes any process that could introduce free reactive groups, attach free reactive groups, or create free reactive groups from existing molecules. The free reactive groups are preferably at or near the top of the surface of the substrate, such that the free reactive groups are accessible to additional chemistry. "Introducing" free reactive groups is any means of producing or generating free reactive groups and includes, but is not limited to, the creation or formation of free reactive groups, or the transformation of other chemical groups into free reactive groups. The means of producing or generating a free reactive group on the substrate can be chemical, mechanical or any combination thereof. For example, the free reactive groups may be covalently bound to the substrate. For the purposes of treating the substrates, the terms "form" or "introduce" are used interchangeably herein. As used herein, a free reactive group is well understood in the art. Thus, a free reactive group is simply a chemical group that is capable of reacting with a second chemical group. The free reactive group may itself be an entire chemical entity or it may be a portion of an entire chemical entity, including, but not limited to single atoms or ions. Further, the second group with which the free reactive group is capable of reacting can be the same as or different from the free reactive group. Examples of free reactive groups that can be formed include, but are not limited to, halogens, amines, amides, aldehydes, vinyls, hydroxyls and carboxyls.

Treatment processes include, but are not limited to, such processes as cleaning glassware, comprising the use of water, that would form free reactive groups on the surface of the glass. Furthermore, cleaning the glass substrate would remove substantially all organic contaminants that may be present on the surface of the glass.

Another example of a treatment process would include plasma cleaning of metal and non-metal substrates, such as silicon, glass, and plastic to remove substantially all organic contaminants, as well as form or create free reactive groups, such as hydroxyl groups, at or near the surface of the substrate. In plasma cleaning, a gas, such as oxygen, is exposed to an energy source, such as an electric field, to produce ions and free radicals or other reactive species. The plasma cleaning may, but need not, take place in the presence of a vacuum, the presence of which would affect the temperature at which the plasma cleaning would occur. One of ordinary skill in the art will recognize and understand the plasma cleaning procedures and appreciate that, in general, the presence of a vacuum during the plasma cleaning processes will lower the temperature at which the cleaning takes place. Gases used in conjunction with the plasma treatment include, but are not limited to, oxygen, air, ammonia, argon, nitrogen, an oxygen/carbon tetrachloride ($CF_4$) mixture, and any combination thereof. The precise chemical makeup of the gas or gases used in the plasma cleaning is a matter of routine optimization to one of ordinary skill in the art. The temperature at which the plasma cleaning will take place is also a matter of routine optimization and can vary, depending on such conditions as the presence of a vacuum or the composition of the substrate. In general, however, the temperature at which the plasma cleaning takes place is from about 15° C. to about 200° C. In particular, the temperature range is from about 25° C. to about 50° C. The plasma generating electrical power density at which the cleaning will take place is also a matter of routine optimization, and may vary. In general, however, the power density at which the plasma cleaning takes place is from about 0.1 Watts/Liter (W/L) to about 10 W/L. In particular, the power density is 1 about W/L. The pressure at which the cleaning will take place is also a matter of routine optimization, and may vary. In general, however, the pressure at which the plasma cleaning takes place is from about 1 mTorr to about 1 atmosphere. In particular, the pressure is from about 10 mTorr to about 500 mTorr. The duration of the cleaning process is a matter of routine optimization, and may vary. In general, however, the duration of the plasma cleaning is from about 1 second to about 60 minutes. In particular, the duration is from about 20 seconds to about 240 seconds.

Referring to FIG. 1, treated substrate 1 has deposited thereon a monomer layer 2a. Subsequent bioactive surface 3a can be covalently coupled to layer 2a as described herein.

Figure 2:
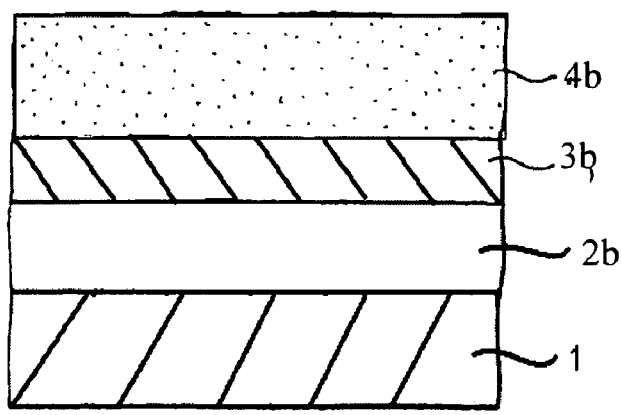
FIG. 2 depicts a side-view of an embodiment of an article of the present invention, comprising a substrate (1), a hydroxyl-rich layer (2b), a deposited monomer layer (3b), and a bioactive surface (4b).

Still another example of a treatment process would include coating the substrate with a polymer that is rich with the desired free reactive group. For example, if the desired free reactive group is hydroxyl, a hydroxyl-rich polymer, such as, but not limited to, hydroxyethyl methacrylate (polyHEMA) can be coated onto the surface. For example, referring to FIG. 2, polyHEMA could be dissolved in ethanol and deposited onto the surface of substrate 1. The ethanol would, in turn, evaporate and leave a thin hydroxyl-rich polymer layer 2b behind. The formed hydroxyl-rich layer 2b can be further modified by plasma deposition of "monomer-rich" or "group-rich" layer 3b. Coupling of bioactive surface 4b to layer 3b constitutes an embodiment as described herein.

Another example of a treatment process is the crosslinking of monomers on the substrate. For example, any of the aforementioned plasma cleaning parameters may be optimized to crosslink, for example, HEMA monomers to create a polyHEMA-rich layer on the substrate. The crosslinked HEMA monomers on the substrate may still form hydroxyl rich layers on the surface of these substrates.

Any of the treatment processes can be combined with one another to treat the substrate, such that "treating" a substrate would include one or more treatment processes. The treatment processes may be carried out sequentially, concurrently, or combinations of sequential and concurrent processes. For example, a glass substrate may be treated using water and plasma cleaning treatments. Further, the type of treatment may depend on the substrate that is being treated. For example, although effective, plasma treatment may not be the optimal treatment process to use on plastic substrates. In contrast, plasma treatment may be ideal for glass and metal substrates. In referring again to FIG. 1, plasma treatment of substrate 1 may alternately include the co-plasma deposition of, or sequential deposition of, monomers of HEMA and alkoxyaminoalklysilanes, depicted as layer 2a. Subsequent bioactive surface 3a can then be covalently coupled to layer 2a as described herein.

In another embodiment, methods of the current invention require the deposition of a monomer onto the treated substrate. The deposition of the monomer may result in the formation of at least one monolayer on the substrate, or it may result in a polymerized monomer layer on the substrate. The deposition of the monomer may also result in formation of several monolayers on the substrate. The deposition and treatment processes of the methods described herein can be performed simultaneously or separately. A "monomer-rich substrate" or "group-rich substrate" is used to indicate that the substrate, after the deposition, comprises more of the desired monomers, or chemical groups thereof, than are ordinarily found on the surface of the substrate, regardless of the state of polymerization of the monomer or chemical group, after the deposition. Along those same lines, a "monomer-deposited substrate" or "a monomer that has been deposited" are used to indicate that a monomer was deposited onto a substrate, regardless of its state of polymerization after the deposition onto the surface. Thus, an embodiment of the invention described herein encompasses methods where the surface of the substrate may or may not comprise the desired monomer, or chemical groups thereof, prior to beginning the preparation methods or the deposition processes. The monomers may comprise chemical groups that include, but are not limited to, amines ($—NH_2$), halogens such as chloro (—Cl), sulfhydryls (—SH), epoxide, glycidyl, cyano (CN), acrylate, and vinyl ($—CH=CH_2$). In one embodiment, the monomer that is deposited comprises an amine group. To be clear, an "amine-rich substrate", for example, is used to mean a substrate that, after the deposition, comprises more amine groups than are ordinarily found on the surface of the substrate. The monomer that is used in the deposition process may be, for example, any alkoxysilane, wherein the silane monomer is terminated with the chemical group, such as an amine ($—NH_2$), chloro (—Cl), sulfhydryl (—SH), carboxyl (—COOH), epoxide, glycidyl, cyano (CN), acrylate, and vinyl ($—CH=CH_2$). The choice of monomer will depend on the desired group that will enrich the substrate.

The "monomer-deposited substrates" of the present invention can be two-dimensional or three-dimensional. The terms "two dimensional" and "three-dimensional" are used as they are in the art, and are generally used to mean a flat, structureless substrate or a non-flat structure, respectively. The methods of the present invention include processes for imparting three-dimensionality to the monomer-deposited substrates, prior to the addition of the biologically functional molecules. Accordingly, if three-dimensionality were imparted to the monomer-deposited substrate, e.g., a silane-deposited substrate, then, for the purposes of the present invention, the "monomer-treated substrate" would comprise the three-dimensional structure.

In one embodiment of the present invention, an amine-terminated silane is deposited onto the treated substrate. In this instance, the substrate would be considered a "silane deposited" substrate. Amino-terminated silanes are of the general formula $NH_2—R—Si—(OR')_n$, wherein R is a lower aliphatic group, R' is and/or the same or different lower alkyl or phenyl groups, and n is 1, 2 or 3. In one embodiment, R' is methyl and n is 3. It will be understood that substitution can occur at the amino group when the amino-functional silane includes a polymeric or oligomeric backbone, which may itself include repeating amino moieties. Exemplary amino-functional silanes include, but are not limited to, N-(2-aminoethyl-3-aminopropyl)trimethoxy silane, 3-aminopropyltriethoxy silane (APTES), and 3-aminopropyltrimethoxy silane (APTMS). An example of an amino-functional polymeric silane is N-(trimethoxysilylpropyl) polyethyleneimine, which is a trimethylsilylpropyl substituted polyethyleneimine.

The deposition of the monomer that results in a "monomer-rich substrate" or "group-rich substrate" is performed in a solvent-free environment. A "solvent-free environment" is used herein to mean that the substrate on which the monomer to be deposited does not interact with a liquid phase during the deposition process. In other words, the deposition of the monomer involves methods other than those that utilize the liquid phase, like dipping or coating the substrate in or with a liquid. Solvent, however, can be used in other parts of the methods described herein. As is well understood in the art, a "solvent" is used herein to mean any aqueous-based or organic-based liquid with or without solute. Examples of organic solvents include, but are not limited to, water and alcohols such as ethanols, methanol and isopropanol. Example of a solvent free environment includes without limitation, vapor phases, supercritical phases, and plasma phases of compounds.

The deposition processes can be any process that results in the deposition of a monomer, provided liquid solvent does not come into contact with the substrate. The deposition of the monomer may, but need not, result in the polymerization of the monomer being deposited. Thus, in all of the embodiments of the inventions described herein, the deposition of the monomer may or may not result in forming a polymerized monomer layer. Common example of such processes includes without limitation, chemical vapor deposition, physical vapor deposition, or a combination of physical and chemical vapor deposition that includes, but is not limited to, physical enhanced chemical vapor deposition. In general, vapor deposition, either chemical or physical, is the transformation of gas molecules into a solid film or layer.

In general, chemical vapor deposition is a process whereby the molecules or chemical groups to be deposited are formed in a chemical reaction (or reactions) between gaseous reactants, at elevated temperatures, near the surface substrate. Examples of chemical vapor deposition include, but are not limited to, plasma enhanced chemical vapor deposition (PEVD), atmospheric pressure chemical vapor deposition (APCVD), low pressure chemical vapor deposition (LPCVD), photochemical vapor deposition (PCVD), laser chemical vapor deposition (LCVD), metal-organic chemical vapor deposition (MOCVD), chemical beam epitaxy (CBE) and chemical vapor infiltration (CVI).

In a typical chemical vapor deposition process, reactant gases, which can be diluted in a carrier gas, enter a reaction chamber at room temperature and can be heated as it approaches the deposition substrate. The gas or gas mixture can itself be heated, or the gas or gas mixture can be placed upon a heated substrate. The temperature at which the plasma deposition will take place is a matter of routine optimization and can vary, depending on such conditions as the presence of a vacuum or the composition of the substrate. In general, however, the temperature at which the plasma deposition takes place is from about 15° C. to about 200° C. In particular, the temperature range is from about 25° C. to about 50° C. The plasma generating electrical power density at which the deposition will take place is a matter of routine optimization, and may vary. In general, however, the power density at which the plasma deposition takes place is from about 0.1 Watts/Liter (W/L) to about 10 W/L. In particular, the power density is 1 about W/L. The pressure at which the deposition will take place is a matter of routine optimization, and may vary. In general, however, the pressure at which the plasma deposition takes place is generally from about 1 mTorr to about 1 atmosphere. In particular, the pressure is from about 10 mTorr to about 500 mTorr. The duration of the deposition process is a matter of routine optimization, and may vary. In general, however, the duration of the plasma deposition is from about 1 second to about 60 minutes. In particular, the duration is from about 20 seconds to about 240 seconds. Depending on the process and operating conditions, the reactant gases may undergo homogeneous chemical reactions in the vapor phase before striking the substrate.

Physical vapor deposition typically includes bombarding the substrate with plasma that comprises the chemical group to be deposited. Typically, an energy source is directed towards a gas to produce gaseous ions or free radicals. Examples of physical vapor deposition include, but are not limited to, vacuum evaporation, ion plating, ion implantation, sputtering and molecular beam epitaxy (MBE).

In one embodiment of the present invention, the deposition process comprises plasma enhanced chemical vapor deposition (PEVD). Plasma enhanced chemical vapor deposition is a type of chemical vapor deposition wherein the monomer or chemical group to be deposited is made chemically reactive due to the action of various energetic species formed in the plasma, such as high-energy electrons, positive and negative ions, high-energy photons, metastables, and radicals.

The methods of the current invention also preferably include immobilization of biologically functional molecules onto the "group-rich" substrates. The methods of the present invention do not require the biologically functional molecules and the monomers to be in solution together, although they may be. Any molecules that can react with the chemical groups deposited on the substrate and are capable of rendering the surface of the article biocompatible and/or bioactive are considered to be "biologically functional molecules." As used herein, a "biocompatible molecule" is any molecule that is capable of rendering the surfaces biocompatible, and is to be considered a biologically functional molecule. As used herein, a biocompatible surface is a surface that is stable in a biological environment, resistant to cell adhesion and fouling, and does not initiate any appreciable immunogenic response in an in vivo setting. Likewise, a molecule that is "bioactive" is also to be considered a biologically functional molecule. As used herein, a bioactive molecule is any molecule that is capable of specific interaction with a target molecule or ligand, such as, but not limited to, a binding molecule, a receptor, an antibody, or an enzyme. Example of biologically functional molecules include, but are not limited to, monosaccharides, disaccharides, polysaccharides, amino acids, oligopeptides, polypeptides, proteins, proteoglycans, glycoprotein, nucleic acids, oligonucleotides, polynucleotides, lipids, fatty acids, other natural or synthetic polymers, and small molecular weight compounds such as drugs or drug candidates. Specific examples of biologically functional molecules that render the surfaces biocompatible include, but are not limited to, hyaluronic acid (HA), alginate (AA), polyethylene glycol (PEG), hydroxyethyl methacrylate, polylactide, polyglycolic acid, methacrylate, acrylate, and copolymers thereof. Specific examples of copolymers include methacrylate-hydroxyethyl methacrylate, acrylate-hydroxyethyl methacrylate, and acrylate-methacrylate-hydroxyethyl methacrylate copolymers. Specific examples of biologically functional molecules that render the surfaces bioactive include, but are not limited to, extracellular matrix molecules, such as collagen and laminin, anticoagulants, such as heparin or heparan sulfate, antibodies, and fragments thereof, enzymes or fragments thereof, and binding molecules, such as periplasmic binding proteins (PBPs), luminescent labeled periplasmic binding proteins (PBPs), or fragments thereof. A biologically functional molecule may be capable rendering the surface of an article biocompatible and bioactive at the same time. Also, more than one type of biologically functional molecule may be immobilized onto an embodiment of an article of the invention. For example, an article of the present invention may comprise one biologically functional molecule attached to the monomer-deposited substrate to render the surface of the article biocompatible, in addition to a different biologically functional molecule attached to the monomer-deposited substrate to render the surface of the article bioactive. In such a situation, only one of the biologically functional molecules must be covalently attached to the monomer-deposited substrate. Any additional biologically functional molecule can be attached either directly, though covalent attachment of the molecule to the monomer-deposited substrate, or indirectly, such as by covalent attachment of one biologically functional molecule to another. The indirect attachment of one biologically functional molecule to another can be covalent or non-covalent, provided that at least one of the biologically functional molecules is covalently attached to the monomer-deposited substrate. For example, a drug or other compound can be encapsulated, and this encapsulated drug or compound can be attached to the monomer-deposited substrate to prepare a controlled release device. The nature of the attachment of the biologically active molecules to one another may depend on the conditions or use of the article. For example, an article comprising a monomer-deposited substrate may be used in a controlled release setting, such that covalent attachment of a biologically active agent to another biocompatibility agent may not be desired or practical.

As used herein, a "PBP" is a periplasmic binding protein characterized by its three-dimensional configuration (tertiary structure), rather than its amino acid sequence (primary structure) and is characterized by a lobe-hinge-lobe region. The PBP will normally bind an analyte specifically in a cleft region between the lobes of the PBP. Furthermore, the binding of an analyte in the cleft region will then cause a conformational change to the PBP that makes detection of the analyte possible. Periplasmic binding proteins include any protein that possesses the structural characteristics described herein; and analyzing the three-dimensional structure of a protein to determine the characteristic lobe-hinge-lobe structure of the PBPs is well within the capabilities of one of ordinary skill in the art. Examples of PBPs include, but are not limited to, glucose-galactose binding protein (GGBP), maltose binding protein (MBP), ribose binding protein (RBP), arabinose binding protein (ABP), dipeptide binding protein (DPBP), glutamate binding protein (GluBP), iron binding protein (FeBP), histidine binding protein (HBP), phosphate binding protein (PhosBP), glutamine binding protein, oligopeptide binding protein (OppA), or derivatives thereof, as well as other proteins that belong to the families of proteins known as periplasmic binding protein like I (PBP-like I) and periplasmic binding protein like II (PBP-like II). The PBP-like I and PBP-like II proteins have two similar lobe domains comprised of parallel β-sheets and adjacent α helices. The glucose-galactose binding protein (GGBP) belongs to the PBP-like I family of proteins, whereas the maltose binding protein (MBP) belongs to the PBP-like II family of proteins. The ribose binding protein (RBP) is also a member of the PBP family of proteins. Periplasmic binding proteins disclosed above include, but are not limited to, luminescent labeled periplasmic binding proteins. The luminescent label is any molecule or fragment thereof attached to the binding protein, the label being capable of a detectable change of its wavelength, intensity, lifetime, energy transfer efficiency, and/or polarization upon binding of analyte to the protein, including any change in analyte concentration, when interrogated with light.

As used herein, the term "antibody" is used to refer to any antibody-like molecule that has an antigen binding region, including but not limited to antibody fragments, such as Fab', Fab. F(ab')$_2$, single domain antibodies (DABs), Fv, scFv (single chain Fv), linear antibodies, diabodies, and the like. The techniques for preparing and using various antibody-based constructs and fragments are well known in the art (see Kabat et al., "Sequences of Proteins of Immunological Interest" 5th Ed., Public Health Service, National Institutes of Health, Bethesda, Md., (1991), which is herein incorporated by reference). Diabodies, in particular, are further described in EP 404,097 and WO 93/11161, each of which is incorporated herein by reference; whereas linear antibodies are further described in Zapata et al., Protein Eng., 8(10):1057-1062, (1995), which is herein incorporated by reference.

As used herein, an "enzyme or fragment thereof" includes the portion of an enzyme that is responsible for specifically recognizing a substrate or analyte. The enzyme or fragment thereof need not be possess catalytic activity, provided that the enzyme or fragment thereof can recognize an analyte or substrate with at least some specificity.

The immobilization of the biologically functional molecules onto the "group-rich" substrate includes typical chemical reactions that are well-known in the art. The immobilization is through covalent bonding, via any reaction that results in covalent bonding. Thus any chemistry, e.g., EDC/NHS carbodiimide chemistry, that results in the covalent immobilization of the molecule is within the contemplated scope of the present invention. Examples of chemical reactions include, but are not limited to, condensation, hydrolysis, conjugation, redox, and reductive amination reactions. The type of chemical reaction used to immobilize the molecules is not critical, provided the reaction is designed to covalently immobilize the molecule onto the group-rich substrate. For example, an oxidized polysaccharide containing an aldehyde (—COH) can be covalently immobilized to an amine-rich substrate via a reductive amination reaction that utilizes a strong reducing agent, such as cyanoborohydride.

The method embodiments of the current invention may also include an optional process of imparting three-dimensional structure to the substrate or any subsequent layer, prior to or in conjunction with the covalent immobilization of the functional molecules. The formation of a three-dimensional structure on or in conjunction with the monomer-deposited substrate can be accomplished by the addition of a covalently bound compound or compositions that imparts such structure. The substance that imparts three a three-dimensional structure onto the substrate may be biologically functional as defined herein. For example, compounds or compositions that are capable of imparting three-dimensional structure to the monomer-deposited substrate include, but are not limited to, alginate, hyaluronic acid, polylactide, polyHEMA, polyglycolic acid, polyethylene glycol, and acrylate, or co-polymers thereof. The substance that imparts the three-dimensional structure onto the substrate can attached to the monomer-deposited substrate through covalent bonding and can be attached through any type of reaction designed to covalently attach the substance to the monomer-desposited substrate. The "three dimensionality" imparted onto the substrates can include a porous or lattice-type structure that could be used to, for example, increase the surface area of the monomer-deposited substrate or to create an environment for the controlled-release of substances such as drugs. To that end, drugs or other compounds may be encapsulated and the encapsulated drugs or compounds could be indirectly attached to the coated porous or non-porous monomer-deposited substrate. Examples of encapsulating materials useful for encapsulating compounds include, but are not limited to, polymers or copolymers of lactic and glycolic acids, or mixtures of such polymers and/or copolymers, commonly referred to as "polylactides."

For example, the compounds that are attached directly or indirectly to the monomer-deposited substrate can be formulated according to known methods to prepare pharmaceutically useful compositions, whereby these materials, or their functional derivatives, are combined in admixture with a pharmaceutically acceptable carrier vehicle. Suitable vehicles and their formulation, are described, for example, in Remington's Pharmaceutical Sciences (16th ed., Osol, A., Ed., Mack, Easton Pa. (1980)). To form a pharmaceutically acceptable composition suitable for effective administration, such compositions will contain an effective amount of agent together with a suitable amount of carrier vehicle.

Additional pharmaceutical methods may be employed to control the duration of action. Control release preparations may be achieved through the use of polymers to complex or absorb the agent. The controlled delivery may be exercised by selecting appropriate macromolecules (for example polyesters, polyamino acids, polyvinyl, pyrrolidone, ethylenevinylacetate, methylcellulose, carboxymethylcellulose, or protamine, sulfate) and the concentration of macromolecules as well as the methods of incorporation in order to control release. Another possible method to control the duration of action by controlled release preparations is to incorporate the compound into particles of a polymeric material such as polyesters, polyamino acids, hydrogels, poly(lactic acid) or ethylene vinylacetate copolymers. Alternatively, instead of incorporating these agents into polymeric particles, it is possible to entrap these materials in microcapsules prepared, for example, by coacervation techniques or by interfacial polymerization, for example, hydroxymethylcellulose or gelatine-microcapsules and poly(methylmethacylate) microcapsules, respectively, or in colloidal drug delivery systems, for example, liposomes, albumin microspheres, microemulsions, nanoparticles, and nanocapsules or in macroemulsions. Such techniques are disclosed in Remington's Pharmaceutical Sciences (1980).

Articles according to preferred embodiments of the present invention, three dimensional or not, may be used as biosensors. For example, a glucose sensor can be prepared at one end, e.g. the distal end, of an optical fiber, while the other end is coupled to a fluorescence detection device, see U.S. pending application Ser. No. 10/721,797, filed Nov. 26, 2003, which is herein incorporated by reference. At least a portion of the sensing (distal) end of the fiber can be first coated with a monomer, such as APTMS, as in Example 1 below; and a polymer matrix, such as alginate, can then be coupled to the monomer layer. A biologically functional molecule, such as a "sensing element," for example a glucose binding protein including but not limited to glucose oxidase or glucose-galactose binding protein, can, in turn, be covalently bound to or entrapped within the alginate. In one specific embodiment, the sensing a periplasmic binding protein that comprises a luminescent label. See example 3 below.

In one embodiment, a glass fiber is used in a biosensor and comprises a silica core, silica cladding, and polyimide buffer. The fiber diameter can be from about 100 µm to about 750 µm. In particular, the fiber diameter can be about 400/440/470 µm, where the slashes denote diameters measured from the core/cladding/buffer exteriors, respectively.

Another embodiment also relates to monomer-deposited substrates or articles comprising bioactive surfaces that have been prepared using the methods described herein. As discussed earlier, the substrate prepared according to the methods of the current invention can be any substrate capable of being prepared. Further, additional embodiments also relate to methods of using the monomer-deposited substrates either alone or as part of an article such as a biosensor. For example, one embodiment of the invention relates to methods of screening the effects of biological agents, or suspected agents, using the monomer-deposited substrates or a article comprising the monomer-deposited substrates that have been prepared according to the methods described herein. Indeed, the monomer-deposited substrates or articles comprising the monomer-deposited substrates may be used to screen the effects of a variety agents that are capable of, or suspected of being capable of, affecting the survival, proliferation and/or differentiation of cells or tissue in an in vitro, in situ, or in vivo environment. As another example, the monomer-deposited substrates or articles comprising the monomer-deposited substrates may be used to screen the effects of drugs or drug candidates on the survival, proliferation and/or differentiation of cells or tissue in an in vitro or in vivo environment. Further, the monomer-deposited substrates or articles comprising the monomer-deposited substrates may be used in methods of treating diseases in subjects in need of treatment thereof. For example, in one embodiment, treatment of cardiovascular disease such as, but not limited to, atherosclerosis, comprises the use of stents or other implants whose surfaces have been prepared according to the methods described herein. These stents or implants would, of course, comprise biologically functional molecules, such as anti-clotting agents. The monomer-deposited substrates or articles comprising the monomer-deposited substrates may also be used in diagnostic or treatment settings such as in dialysis machines. The monomer-deposited substrates or articles comprising the monomer-deposited substrates may be used in methods for sensing certain target molecules such as, for example insulin or glucose, and may thus be used as biosensors. For example, biologically functional molecules that produce a signal in response to binding target molecules may be immobilized to the monomer-deposited substrates. To that end, the biologically functional molecules may be immobilized directly or indirectly to the monomer-deposited substrate. The methods of immobilizing the biologically functional molecules onto the monomer-deposited substrates should not limit the scope of the present invention. The signal could be generated in an in vitro, in situ, or an in vivo environment.

The monomer-deposited substrates prepared by the methods of the present invention preferably possess a substantially uniform thickness of a layer of polymerized monomer on the surface of the substrate. Using traditional wet chemistry methods, such uniformity is not possible to control, predict or replicate in preparing articles having bioactive surfaces. Indeed, traditional wet chemistry techniques for depositing monomers onto surfaces of substrates typically results in an entirely non-uniform coating such that bare, uncoated areas are present throughout the surface. Indeed, a scanning electron micrograph of articles with surfaces prepared according to traditional techniques reveals a "splotchy" and highly uneven morphology. Thus, the thickness of the monomer layer can vary up to 100% (several microns thick versus uncoated) in any given area of the surface, using traditional chemistry. With the present methods, however, the thickness of the monomer layer(s) to which the biologically functional molecules are attached is more uniform. In one embodiment, the thickness of the layer of the polymerized monomers varies less that 70% in any one area compared to another. In particular, the variation between the deposited monomer layer on the same substrate surface may vary less than 60%, less than 50%, less than 40%, less than 30%, less than 20% and even less than 10% or 5%.

The present methods also result in a deposited monomer layer of substantially uniform thickness that can be exceedingly thin. As a corollary, the methods of the present invention allow for the customization of the thickness, or thinness, of the deposited monomer layer. For example, the present methods are capable of depositing layers of polymerized monomers onto substrates with a substantially uniform thickness of about 100 to about 1000 Å. The present methods are also capable of depositing layers of polymerized monomers onto substrate surfaces with a substantially uniform thickness of about 1000 to about 100,000 Å. This layer that is of substantially uniform thickness may, of course, be thicker.

The present methods also result in monomer-deposited substrates or articles comprising the monomer-deposited substrates that are substantially defect-free. The monomer-deposited substrates or articles comprising monomer-deposited substrates prepared by the methods of the present invention possess one or more monomer layers that is/are substantially defect-free. As used herein, a "defect" in a layer or coating is used to mean such unwanted characteristics as pin-holes, inclusions, cracks, voids, etc. Accordingly, the present invention relates to monomer-deposited substrates or articles comprising the monomer-deposited substrates that comprise layers of monomers (which may or may not be polymerized after deposition onto the substrate) that are substantially defect-free and of a substantially uniform thickness. Articles of the present invention having bioactive surfaces exhibit these properties, regardless of the composition of the substrate prior to the methods of the present invention.

Glass and plastic substrates, for example, can be subjected to the methods of the present invention to create a "group-rich", e.g., amine-rich, substrate having a deposited monomer layer of a substantially uniform thickness and that is substantially defect-free, whereupon biologically functional molecules may be immobilized. This highly functionalized monomer-deposited substrate provides a substantially defect-free layer of deposited polymerized monomers for the immobilization of biologically functional molecules. For example, the methods of the present invention can be used to prepare an amine-rich glass surface where the nitrogen: silicon ratio (NSR) of the surface of the prepared glass substrate, prior to the attachment of the biologically functional molecule(s), is at least about 0.40. In particular, the NSR can be about 0.44. In one embodiment, the nitrogen content of the surface of a glass substrate treated with the methods of the present invention, prior to the addition of the biologically functional molecule(s), can be at least about 5.0%, as measured by ESCA as described in herein. In further embodiments, the nitrogen content is at least about 5.0%, 5.5%, 6.0%, 6.5%, 7.0%, 7.5% or 7.7%. In one specific embodiment, the nitrogen content is at least about 5.5%. Articles of the present invention wherein the substrate is glass include, but are not limited to, labware such as cell culture dishes. The particular use of the glass articles prepared according to the present invention should not be construed as a limiting factor in the present invention. Thus, plastic "glassware" is also envisaged within the scope of the present embodiments.

The monomer-deposited substrates or articles comprising the monomer-deposited substrates may also be formed from plastic. Plastics used herein can be made of any polymer including, but not limited to, polypropylene, polycarbonate, polystyrene, polyacrylamide, polyurethane, polyester, cyclic olefinic copolymers, polymethylpentene, and polyethylene. Articles of the present invention comprising a plastic substrate may be labware, such as cell culture flasks, dishes, microtiter plates, etc. Articles comprising a plastic substrate may also be clinical in nature such as tubing, catheters and drug delivery matrices. The plastic substrate may even be used in or for fiber optics. In other words, the use of an article having a plastic substrate should not be construed as a limiting factor in the present invention.

A plastic substrate that has been prepared by the methods of the present invention will possess one or more layers of deposited polymerized monomers that are of a substantially uniform thickness and that are substantially defect-free, whereupon biologically functional molecules may be immobilized.

The monomer-deposited substrates or articles comprising the monomer-deposited substrates may alternately be formed of metal, such as, for example, a stent. The monomer-deposited substrates of the invention or articles comprising the monomer-deposited substrates can also be comprised of other non-metal materials, such as ceramic, silicon and nitinol. Once again, the specific use of the metal or non-metal articles should not be construed as a limitation of the present invention. A metal substrate that has been prepared by the methods of the present invention will possess one or more monolayers that are of a substantially uniform thickness and are substantially defect-free, whereupon additional functional molecules may be immobilized.

One method of analyzing the monomer-deposited substrates of the present invention involve scanning electron microscopy (SEM). Such methods can demonstrate that the methods of the present invention result in monomer-deposited substrates comprising one or layers that are of substantially uniform thickness and are substantially defect-free. For example, substrates having surfaces prepared using the methods of the present invention exhibit vastly different morphologies under SEM when compared to substrates prepared with traditional methods. The differences in the uniformity of thickness of the monomeric layer(s) of the substrates will be readily apparent using SEM. Furthermore, the number of defects, or lack thereof, of the monomer-deposited substrates of the present invention will also be apparent under SEM, and can be readily compared to defects on substrate surfaces prepared using other methods. Accordingly, SEM may be used to analyze articles having monomer-deposited substrates according to the present invention.

The thickness of the deposited monomer layers on the surface of the substrates of the present invention, however, may be so thin as to escape detection with SEM. As stated earlier, the monomer layers on the substrates prepared according to the present invention may be as thin as about 100 to about 1000 Å, or even thinner. In such a situation, defects may be analyzed using atomic oxygen. For example, defects of the deposited monomer layer may be analyzed by using an etching plasma. In the case where the deposited film is more resistant to a reactive constituent of a plasma discharge than the substrate, the exposure of the plasma to the film will make the location of defects apparent, even if the defects are too small to be seen with scanning electron microscopy. The reactive species will pass through any pinholes or other defects and undercut the substrate, causing a gross collapse in the coating(s). This technology follows the teachings of Degroh and Banks in *Journal of Spacecraft and Rockets,* 31 (4): 656-664 (1994), which is hereby incorporated by reference. In Degroh and Banks, atomic oxygen produced in a plasma system is used to discover defects in coatings used on low Earth orbit satellites and space stations.

In one embodiment of the present invention, the monomer-deposited substrates may be optically transparent or near transparent to light of the ultraviolet, visible, near infrared, and infrared regions. It is not essential, however, that the monomer-deposited substrates described herein be optically transparent. As used here, "optically transparent" is used to mean transparent or near transparent. Articles comprising such optically transparent monomer-deposited substrates can be used, for example, as biosensors. The optically transparent substrates prepared by the methods described herein can, for example, be an optical fiber that comprises a substantially uniform monolayer that is substantially defect-free, which can therefore be used as a component of a biosensor. The biologically functional molecules that are covalently immobilized to the monomer-deposited substrate can, for example, comprise a biosensing protein that binds to a target compound and emits a signal in response to binding of the target. The signal generated in conjunction with this bioactive surface could then be transmitted via the bioactive surface through a optical fiber to a detector/reader.

Figure 3:
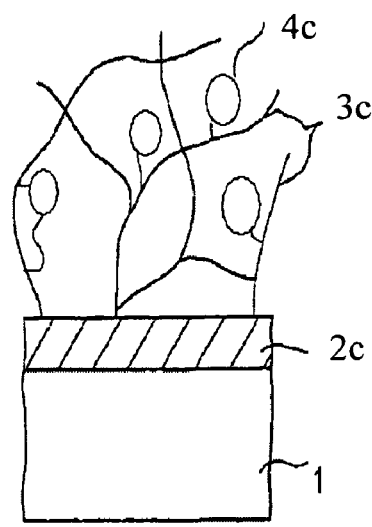
FIG. 3 depicts a side-view of an embodiment of an article of the present invention, comprising a substrate (1), a deposited layer of monomer (2c), and a bioactive surface (3c) with sensing elements (4c).

In other embodiment, a sensing element comprising a biologically functional molecule such as a biosensing protein, is immobilized or encapsulated in a water-insoluble crosslinked polymeric bioactive surface. The crosslinked polymeric bioactive surface can be covalently coupled to an optical fiber having plasma-deposited thereon an amino containing silane. As used herein, the term "crosslinked polymeric bioactive surface" may be any two dimensional or three-dimensional structure that is substantially water insoluble and permeable to an analyte or ligand of interest. The crosslinked polymeric bioactive surface may optionally prevent substantial interference from other biomolecules and may be substantially biocompatible. In one embodiment, the crosslinked polymeric bioactive surface allows the binding protein to retain some degree of conformational and/or orientational mobility. The crosslinked polymeric bioactive surface may consist of multiple layers, with an inner layer serving to retain the binding protein, and one or more outer layers to control the permeability and/or achieve biocompatibility. For example, the crosslinked polymeric bioactive surface may be comprised of any one of those described in co-pending, commonly owned U.S. Pregrant Applications 2003-0153026 and 2004-0234962, the entire contents of which are incorporated herein by reference. The immobilization may be accomplished either by covalently linking the sensing element to the crosslinked polymeric bioactive surface or by physically entrapping the sensing element within the crosslinked polymeric bioactive surface. In the instance where the crosslinked polymeric bioactive surface physically entraps the sensing element, the crosslinked polymeric bioactive surface pores are sized to retain the sensing element. Referring to FIG. 3, which depicts one embodiment where the sensing element 4c is attached to the crosslinked polymeric bioactive surface 3c, where surface 3c is attached to deposited monomer layer 2c, and deposited monomer layer 2c is attached to substrate 1. In one embodiment, the sensing element 4c is attached to the crosslinked polymeric bioactive surface 3c using, for example, covalent or ionic linkages.

Articles comprising bioactive surfaces of the present invention may also exhibit a quicker reaction time, in response to changing condition in the biological environment. The methods of the present invention allow for the preparation of articles comprising monomer-deposited substrates with monomer layers that are thinner than monomer layers prepared with traditional techniques. Without being bound by theory, the thinness of the monomer layer(s) on of the monomer-deposited substrates of the present invention may permit a quicker diffusion time across the monomer layer, allowing quicker reaction times in response to changes in the immediate environment.

Thus, an optical fiber glucose biosensor having a bioactive surface prepared according to the methods described herein enabled the detection of analyte (for example, glucose) with a rapid response and recovery time. In particular, a glucose biosensor exposed to solutions of varying glucose concentrations in such biological environments as buffer, blood plasma and whole blood, fully responded in less than 30 seconds to increases in glucose concentrations, and fully responded in under 3 minutes to decreases in glucose concentrations.

The examples described herein are for illustrative purposes and are, in no way, intended to limit the scope of the present invention.

EXAMPLES

Example 1

Deposition of Amine-Containing Silane onto Glass Substrates

The plasma treatment process to coat glass samples with polymerized monomer occurred in a 12-inch diameter by 18-inch tall upright cylindrical vacuum chamber. Glass samples were placed on a radio frequency powered 8-inch diameter electrode located at midplane of the chamber. An open 1-inch diameter by 2-inch tall vial containing about 5 cubic centimeters of APTMS was placed on the electrode. The system was initially evacuated by a turbomolecular pump, backed with a rotary vane roughing pump, to a pressure of about 8 milliTorr. The valve in the pumping line was then throttled back to allow the pressure of the vaporizing monomer to rise to a constant 85 milliTorr. The electrode was then excited by a 13.56 MHz radio frequency power generator, in series with a matching network to deliver 22 watts of power. The plasma so produced was operated for 60 seconds to polymerize the monomer vapor into a film on the surface of the glass substrate.

Following treatment, the chamber was vented to atmospheric pressure and the sample was removed. SEM photos showed film thickness of up to about 150 nm on the glass, stainless steel, aluminum and alginate substrates. Electron Spectroscopy Chemical Analysis (ESCA) of the APTMS-deposited substrates revealed that the samples comprised the following elements: oxygen, nitrogen, carbon and silicon. See Table 1.

TABLE 1

ESCA analysis of APTMS Layer on various substrates Compared to the APTMS monomer:

|  | Glass | Stainless Steel | Aluminum | Alginate | Monomer (Calculated) |
| --- | --- | --- | --- | --- | --- |
| Oxygen | 28.3 | 30.3 | 32.4 | 31.4 | 29.6 |
| Nitrogen | 5.5 | 6.6 | 6 | 6.9 | 8.6 |
| Carbon | 53.6 | 49.1 | 45.2 | 47.6 | 44.4 |
| Silicon | 12.6 | 14 | 15 | 14.1 | 17.3 |

In comparison, control samples were composed of: oxygen, sodium, potassium, carbon, and silicon. See Table 2. The monomer itself is 44.4% carbon, 29.6% oxygen, 8.6% nitrogen and 17.3% silicon, excluding hydrogen, as ESCA typically does.

TABLE 2

ESCA analysis of bare surface controls without APTMS Layer compared to the monomer:

|  | Glass | Stainless Steel | Aluminum | Alginate | Monomer (calculated) |
|---|---|---|---|---|---|
| Oxygen | 41.3 | 32.8 | 29.5 | 33 | 29.6 |
| Nitrogen |  | 3.1 | 2.1 | 7.2 | 8.6 |
| Carbon | 33 | 41.4 | 54.3 | 56.2 | 44.4 |
| Silicon | 17.9 | 11.7 |  |  | 17.3 |
| Iron |  | 9 |  |  |  |
| Chromium |  | 1 |  |  |  |
| Calcium |  | 1 |  |  |  |
| Aluminum |  |  | 9.2 |  |  |
| Magnesium |  |  | 4.9 |  |  |
| Sodium | 6 |  |  |  | 3.7 |
| Potassium | 1.9 |  |  |  |  |

Example 2

Preparation of a Non-Fouling Surface on Glass-Bottom Plates

BD Labware 96 well glass-bottom plates (catalog #3537311) were exposed to an APTMS plasma as described in Example 1. A bioactive surface comprising polysaccharide (hyaluronic acid, Lifecore Biomedical) was subsequently covalently attached to the plasma coated surface of half of the wells of the plates using an aqueous EDC/NHS carbodiimide coupling chemistry. MC3T3 cells (mouse, osteoblast cells) were seeded into every well of the 96 well plate at 10,000 cells/well in 200 μL alphaMEM media containing 10% FBS. The section of the plate coated only with the APTMS showed significant cell adhesion and growth by 48 hours. The half of the plate coated with HA-coupled to the APTMS surface did not allow cells to attach within the same 48 hours. Thus, attachment dependent cells were unable to attach and therefore, could not grow or spread on the culture plate surface prepared in accordance with the methods herein described. Thus, the surface prepared by this method and thus the article was rendered non-fouling.

It is understood that this method is envisaged for use for culture dishes, disposable plates, and other cell or tissue vessels and apparatuses, and this method is readily adaptable for covalent immobilization of proteins, antibodies, peptides, drugs, or small molecules to surfaces, fibers, biosensors, micro- and nano-particles.

Example 3

Preparation of a Glucose Biosensor

A glucose sensor was prepared at one end of a 400 μm core diameter optical fiber while the other end was coupled to a fluorescence detection device. The polished sensing end of the fiber was coated with APTMS as in Example 1. A bioactive surface comprising an alginate-based hydrogel matrix was coupled to the APTMS layer. The alginate hydrogel matrix was prepared by covalently cross-linking Pronova™ UP LVG alginate through the carboxyls with adipic acid dihydrazide (AAD), via carbodiimide chemistry. Pronova™ UP LVG was selected its low viscosity and high guluronic to mannuronic ratio. A 2% alginate solution was prepared by dissolving 1 gram of alginate into 50 mL 0.1 M MES buffer (pH 6.0) and adding 110 mg of AAD and 79 mg of hydroxybenzotriazole (HOBt). The solution can be stored at 4° C. until needed. To the alginate solution, 145 mg of 1-ethyl-3-(3-dimethylamino-propyl) carbodiimide (EDC) was added per 10 mL of solution, using a dual-syringe mixing technique. The alginate/AAD/HOBt,/EDC mixture was aspirated into a 1 mL syringe with a 30 gauge needle attached. The needle was primed, and then the tip, with a small bead of alginate, was touched to the APTMS coated optical fiber tip. The matrix was allowed to cross-link for about 2-5 minutes. The fiber tip and matrix assembly were transferred to a hydration chamber, where they were stored for 2 hours. At the end of the two hours, the sensing tips were placed in excess pH 8.5 ethanolamine for 15 minutes to quench the reaction.

To attach the binding protein sensing element, the tips were incubated in a solution of fluorescently labeled glucose-galactose binding protein (GGBP) in PBS buffer (53 uM, 50 uL) for approximately 2 hours. The GGBP used in this biosensor was a mutant GBP, wherein a cysteine was substituted for an glutamic acid at position 149, an arginine was substituted for an alanine at position 213 and a serine was substituted for leucine at position 238 (E149C/A213R/L238S). The mutant GGBP protein was labeled at the 149 position with N-((2-iodoacetoxy)ethyl)-N-methyl)amino-7-nitrobenzoxadiazole (IANBD). See U.S. Published Application No. 20030134346A1, incorporated by reference in its entirety. It should be noted, however, that many other mutated and labeled proteins may be used, for example, U.S. Pat. No. 6,277,627, and U.S. Pat. No. 6,855,556, which are incorporated by reference. The sensors were shielded from ambient light during incubation. After 2 hours of incubation, 50 uL of a solution of 1-ethyl-3-(3-dimethylaminopropyl)carbodiimide (EDC)/N-hydroxysulfosuccinimide (sulfo-NHS) (200 mM/50 mM Sigma/Fluka) was then added to the incubation tube. After 40 minutes, the sensor tips were removed and placed in 50 uL of 1M, pH 8.5 ethanolamine to quench the reaction. After 20 minutes in the ethanolamine solution, the sensor tips were transferred to PBS solution, where they were allowed to sit for at least 8 hours while any unreacted protein diffused out. The sensors were then transferred to fresh PBS and stored in the dark until ready to use.

The glucose biosensor of Example 3 responded to changes in glucose concentrations in buffer, blood plasma and whole blood. The glucose values for the buffer and plasma samples were confirmed by a YSI clinical glucose analyzer. The whole blood samples (except 30 mM) were checked with an Accuchek Glucometer. All baseline solutions of 0 mM glucose are in PBS buffer. The glucose concentrations used are millimoles (mM).

What is claimed is:

1. An article comprising a bioactive surface, said article comprising:
   a) a glass substrate, wherein the glass substrate comprises a hydroxyl-rich polymer layer comprising free reactive groups;
   b) an aminopropyltrimethoxysilane (APTMS) layer on top of said hydroxyl-rich polymer layer, wherein said APTMS layer is of substantially uniform thickness and is substantially defect free; and
   c) a biologically functional molecule covalently attached to said APTMS layer.

2. The article of claim 1, wherein said biologically functional molecule is selected from the group consisting of alginate, hyaluronic acid, polyethylene glycol, hydroxyethyl methacrylate, polylactide, polyglycolic acid and co-polymers thereof.

3. The article of claim 1, wherein said biologically functional molecule is hyaluronic acid.

4. The article of claim 1, wherein said biologically functional molecule imparts a three-dimensional structure on said bioactive surface.

5. The article of claim 1, wherein said hydroxyl-rich polymer layer is hydroxyethyl methacrylate (polyHEMA).

6. The article of claim 1, wherein said article is an optical fiber.

7. The optical fiber of claim 6, wherein said optical fiber has a proximal end and a distal end, and wherein said APTMS layer is present on at least a portion of said fiber distal end.

8. The optical fiber of claim 7, wherein said biologically functional molecule comprises a polymer matrix covalently attached to the optical fiber distal end, wherein said polymer matrix is configured to receive a sensing element for sensing a target analyte in a sample.

9. The optical fiber of claim 8, wherein said polymer matrix is selected from the group consisting of hyaluronic acid (HA), alginate (AA), polyethylene glycol (PEG), hydroxyethyl methacrylate, polylactide, polyglycolic acid, methacrylate, acrylate, methacrylate-hydroxyethyl methacrylate, acrylate-hydroxyethyl methacrylate, acrylate-methacrylate-hydroxyethyl methacrylate and mixtures thereof.

10. A biosensor comprising the optical fiber of claim 8 and a sensing element entrapped in or attached to the polymer matrix.

11. The biosensor of claim 10, wherein said sensing element comprises at least one luminescent labeled periplasmic binding protein.

12. The article of claim 1, wherein said article is a glass tissue culture vessel.

13. The article of claim 1, wherein said article is a stent.

14. A method of making the article of claim 1, comprising:
a) treating said glass substrate to form free reactive groups on the surface of said glass substrate by coating said substrate with a hydroxyl-rich polymer layer, said hydroxyl-rich polymer layer comprises free reactive groups;
b) depositing said APTMS layer onto said treated glass substrate in a solvent-free environment; and
c) covalently attaching a biologically functional molecule onto said APTMS-deposited layer to provide the bioactive surface of said article.

15. The method of claim 14, wherein depositing APTMS layer onto said treated substrate in a solvent-free environment is performed by vapor deposition.

16. The method of claim 15, wherein said vapor deposition is chemical vapor deposition or physical vapor deposition or a combination of chemical and physical vapor deposition.

17. The method of claim 15, wherein said vapor deposition comprises a plasma.

* * * * *